(12) United States Patent
Raja

(10) Patent No.: US 10,929,509 B2
(45) Date of Patent: Feb. 23, 2021

(54) ACCESSING AN INTEROPERABLE MEDICAL CODE

(71) Applicant: Arjuna Raja, Philadelphia, PA (US)

(72) Inventor: Arjuna Raja, Philadelphia, PA (US)

(*) Notice: Subject to any disclaimer, the term of this patent is extended or adjusted under 35 U.S.C. 154(b) by 675 days.

(21) Appl. No.: 15/729,276

(22) Filed: Oct. 10, 2017

(65) Prior Publication Data
US 2018/0032684 A1 Feb. 1, 2018

Related U.S. Application Data

(63) Continuation-in-part of application No. 14/530,795, filed on Nov. 2, 2014, now abandoned.

(60) Provisional application No. 61/901,076, filed on Nov. 7, 2013.

(51) Int. Cl.
| | |
|---|---|
| *G16H 10/60* | (2018.01) |
| *G06F 19/00* | (2018.01) |
| *G06F 21/62* | (2013.01) |
| *H04L 29/06* | (2006.01) |
| *G06F 21/60* | (2013.01) |
| *G16H 20/00* | (2018.01) |

(52) U.S. Cl.
CPC ........ *G06F 19/324* (2013.01); *G06F 19/3475* (2013.01); *G06F 21/6245* (2013.01); *G16H 10/60* (2018.01); *H04L 63/0435* (2013.01); *H04L 63/105* (2013.01); *G06F 21/602* (2013.01); *G06Q 2220/10* (2013.01); *G16H 20/00* (2018.01); *H04L 63/083* (2013.01); *H04L 63/0861* (2013.01)

(58) Field of Classification Search
CPC ... G06F 19/322; G06F 19/3418; G06Q 50/24; G06Q 50/22
See application file for complete search history.

(56) References Cited

U.S. PATENT DOCUMENTS

| | | | | |
|---|---|---|---|---|
| 2007/0239484 A1* | 10/2007 | Arond | ................ | G06Q 10/10 705/2 |
| 2012/0036356 A1* | 2/2012 | Barbat | ................ | G16H 10/65 713/165 |
| 2012/0296675 A1* | 11/2012 | Silverman | ............ | G16H 50/30 705/3 |
| 2015/0081371 A1* | 3/2015 | Tang | ................ | G06Q 10/1095 705/7.19 |

* cited by examiner

*Primary Examiner* — Reginald R Reyes
(74) *Attorney, Agent, or Firm* — Kunzler Bean & Adamson

(57) ABSTRACT

For access medical data, a processor retrieves an interoperable medical code in response to a request to fulfill a medical order. The interoperable medical code includes a decryption map, a patient identifier for patient data, a practitioner identifier for practitioner data, and a medical order identifier for medical order data. The processor identifies from the decryption map at least one access credential required to access one or more of the patient data, the practitioner data, and the medical order data required to fulfill the medical order. The processor further accesses the patient data, the practitioner data, and the medical order data required to fulfill the medical order using the at least one access credential.

16 Claims, 16 Drawing Sheets

140

| Decryption Map
380 |
|---|
| Patient Identifier
305 |
| Practitioner Identifier
310 |
| Medical Order Identifier
315 |
| Order Timestamp
325 |
| Reference Number
335 |
| Transmission Timestamp
340 |

209 
| Entity Bits 297 | Security Bits 299 | ... | Entity Bits 297 | Security Bits 299 |
FIG. 2D
463 
| Credential Identifier 461 | Security Level 427 | Access Credential 465 |
|---|---|---|
| Credential Identifier 461 | Security Level 427 | Access Credential 465 |
| Credential Identifier 461 | Security Level 427 | Access Credential 465 |
| Credential Identifier 461 | Security Level 427 | Access Credential 465 |
FIG. 2E

467

201

| Patient Identifier 305 | | |
|---|---|---|
| Patient Contact Data 421 | Security Level 427 | Credential Identifier 461 |
| Insurance Data 423 | Security Level 427 | Credential Identifier 461 |
| Pharmacy Data 431 | Security Level 427 | Credential Identifier 461 |
| Biometric Data 433 | Security Level 427 | Credential Identifier 461 |
| Identifying Document 435 | Security Level 427 | Credential Identifier 461 |
| Hub Identifier 437 | Security Level 427 | Credential Identifier 461 |

| Practitioner Identifier 310 | | |
|---|---|---|
| Practitioner Biometric Data 439 | Security Level 427 | Credential Identifier 461 |
| Organization Data 441 | Security Level 427 | Credential Identifier 461 |
| Public Contact Data 443 | Security Level 427 | Credential Identifier 461 |
| Private Contact Data 445 | Security Level 427 | Credential Identifier 461 |
| License Data 447 | Security Level 427 | Credential Identifier 461 |
| Hub Identifier 437 | Security Level 427 | Credential Identifier 461 |

FIG. 3B

205 

| Medical Order Identifier<br>315 | | |
|---|---|---|
| Practitioner Notes<br>449 | Security Level<br>427 | Credential Identifier<br>461 |
| Prescription Data<br>451 | Security Level<br>427 | Credential Identifier<br>461 |
| Test Order Data<br>453 | Security Level<br>427 | Credential Identifier<br>461 |
| Test Result Data<br>455 | Security Level<br>427 | Credential Identifier<br>461 |
| Treatment Data<br>457 | Security Level<br>427 | Credential Identifier<br>461 |
| File Data<br>459 | Security Level<br>427 | Credential Identifier<br>461 |

FIG. 3C

ACCESSING AN INTEROPERABLE MEDICAL CODE

CROSS-REFERENCE TO RELATED APPLICATIONS

This is a continuation-in-part application of and claims priority to U.S. patent application Ser. No. 14/530,795 entitled "INTEROPERABLE MEDICAL CODE" and filed on Nov. 2, 2014 for Arjuna Raja, which is incorporated herein by reference, and which claims priority to U.S. Provisional Patent Application No. 61/901,076 filed on Nov. 7, 2013, which is incorporated herein by reference.

FIELD

The subject matter disclosed herein relates to medical codes and more particularly relates to accessing an interoperable medical code.

BACKGROUND

Description of the Related Art

Health care practitioners regularly generate medical orders such as pharmaceutical prescriptions, medical device prescriptions, test orders, procedure orders, and diagnostic orders that must be securely fulfilled by other medical service providers.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which:

FIG. 2D is a schematic block diagram illustrating one embodiment of a security vector;

FIG. 2E is a schematic block diagram illustrating one embodiment of credential data;

FIG. 3A is a schematic block diagram illustrating one embodiment of patient data;

FIG. 3B is a schematic block diagram illustrating one embodiment of practitioner data;

FIG. 3C is a schematic block diagram illustrating one embodiment medical order data;

DETAILED DESCRIPTION

Figure 1:
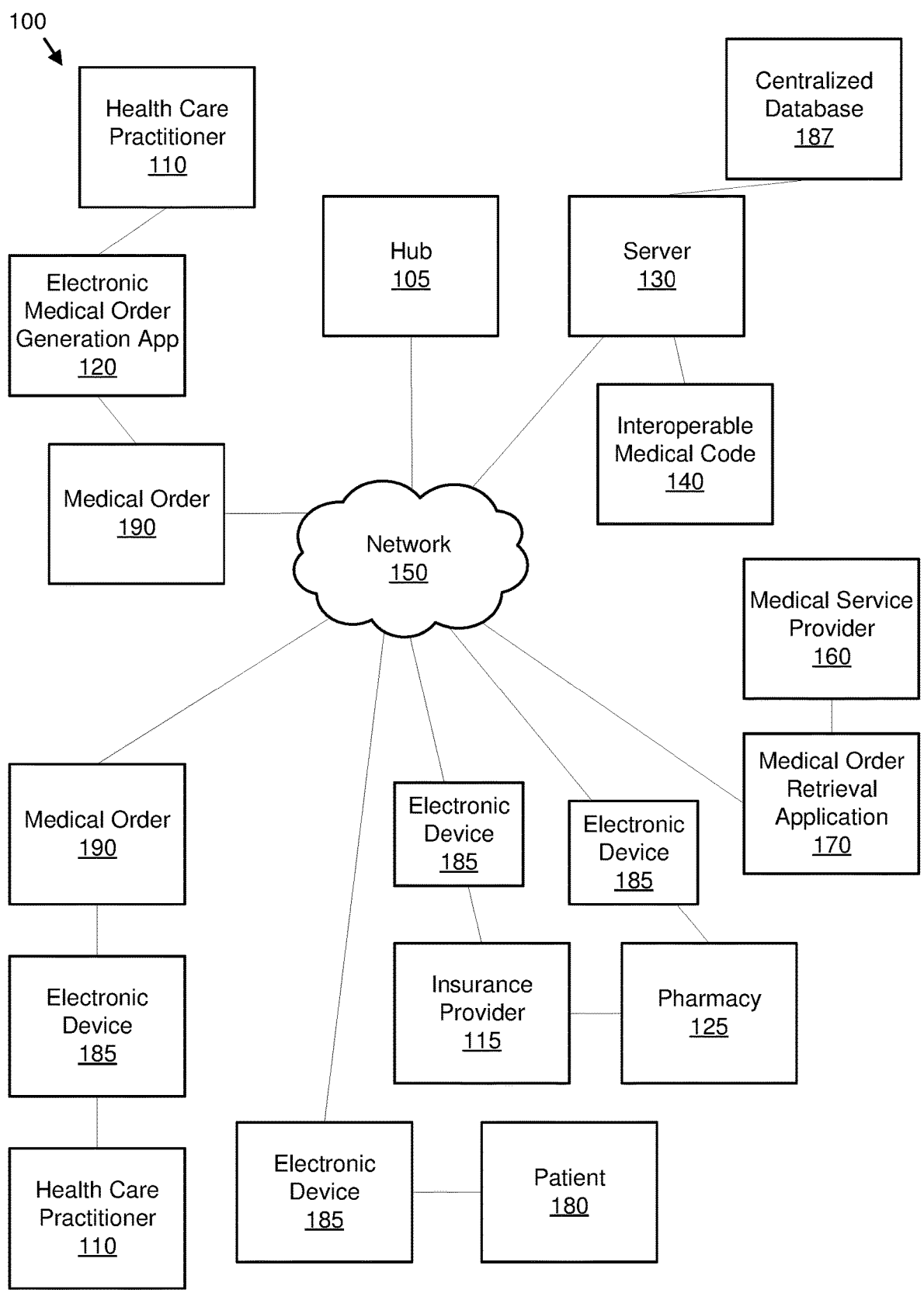
FIG. 1 is a schematic block diagram illustrating one embodiment of an interoperable medical code system.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims, or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including code, program code, firmware, resident software, micro-code, etc.) or an embodiment combining software and hardware aspects that may all generally be referred to herein as a "circuit," "module," or "system." Furthermore, aspects of the present invention may take the form of a computer program product embodied in one or more non-transitory computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer readable medium may be a tangible, non-transitory computer readable storage medium storing the program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store program code for use by and/or in connection with an instruction execution system, apparatus, or device.

The computer readable medium may also be a computer readable signal medium. A computer readable signal medium may include a propagated data signal with program code embodied therein, for example, in baseband or as part of a carrier wave.

Such a propagated signal may take any of a variety of forms, including, but not limited to, electrical, electro-magnetic, magnetic, optical, or any suitable combination thereof A computer readable signal medium may be any computer readable medium that is not a computer readable storage medium and that can communicate, propagate, or transport program code for use by or in connection with an instruction execution system, apparatus, or device. Program code embodied on a computer readable signal medium may be transmitted using any appropriate medium, including but not limited to wireline, optical fiber, Radio Frequency (RF), or the like, or any suitable combination of the foregoing In one embodiment, the computer readable medium may comprise a combination of one or more computer readable storage mediums and one or more computer readable signal mediums. For example, program code may be both propagated as an electro-magnetic signal through a fiber optic cable for execution by a processor and stored on RAM storage device for execution by the processor. Program code for carrying out operations for aspects of the present invention may be written in any combination of one or more programming languages, including an object-oriented programming language such as Python, Java, Smalltalk, C++, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program product may be shared, simultaneously serving multiple customers in a flexible, automated fashion. The computer program product may be standardized, requiring little customization and scalable, providing capacity on demand in a pay-as-you-go model.

The computer program product may be stored on a shared file system accessible from one or more servers. The computer program product may be executed via transactions that contain data and server processing requests that use Central Processor Unit (CPU) units on the accessed server. CPU units may be units of time such as minutes, seconds, hours on the central processor of the server. Additionally, the accessed server may make requests of other servers that require CPU units. CPU units are an example that represents but one measurement of use. Other measurements of use include but are not limited to network bandwidth, memory usage, storage usage, packet transfers, complete transactions etc.

When multiple customers use the same computer program product via shared execution, transactions are differentiated by the parameters included in the transactions that identify the unique customer and the type of service for that customer. All of the CPU units and other measurements of use that are used for the services for each customer are recorded. When the number of transactions to any one server reaches a number that begins to affect the performance of that server, other servers are accessed to increase the capacity and to share the workload. Likewise, when other measurements of use such as network bandwidth, memory usage, storage usage, etc. approach a capacity so as to affect performance, additional network bandwidth, memory usage, storage etc. are added to share the workload.

The measurements of use used for each service and customer are sent to a collecting server that sums the measurements of use for each customer for each service that was processed anywhere in the network of servers that provide the shared execution of the computer program product. The summed measurements of use units are periodically multiplied by unit costs and the resulting total computer program product service costs are alternatively sent to the customer and or indicated on a web site accessed by the customer which then remits payment to the service provider.

In one embodiment, the service provider requests payment directly from a customer account at a banking or financial institution. In another embodiment, if the service provider is also a customer of the customer that uses the computer program product, the payment owed to the service provider is reconciled to the payment owed by the service provider to minimize the transfer of payments.

The computer program product may be integrated into a client, server and network environment by providing for the computer program product to coexist with applications, operating systems and network operating systems software and then installing the computer program product on the clients and servers in the environment where the computer program product will function.

In one embodiment software is identified on the clients and servers including the network operating system where the computer program product will be deployed that are required by the computer program product or that work in conjunction with the computer program product. This includes the network operating system that is software that enhances a basic operating system by adding networking features.

In one embodiment, software applications and version numbers are identified and compared to the list of software applications and version numbers that have been tested to work with the computer program product. Those software applications that are missing or that do not match the correct version will be upgraded with the correct version numbers. Program instructions that pass parameters from the computer program product to the software applications will be checked to ensure the parameter lists match the parameter lists required by the computer program product. Conversely parameters passed by the software applications to the computer program product will be checked to ensure the parameters match the parameters required by the computer program product. The client and server operating systems including the network operating systems will be identified and compared to the list of operating systems, version numbers and network software that have been tested to work with the computer program product. Those operating systems, version numbers and network software that do not match the list of tested operating systems and version numbers will be upgraded on the clients and servers to the required level.

In response to determining that the software where the computer program product is to be deployed, is at the correct version level that has been tested to work with the computer program product, the integration is completed by installing the computer program product on the clients and servers.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and computer program products according to embodiments of the invention. It will be understood that each block of the schematic flowchart diagrams and/or schematic block diagrams, and combinations of blocks in the schematic flowchart diagrams and/or schematic block diagrams, can be implemented by program code. The program code may be provided to a processor of a general-purpose computer, special purpose computer, sequencer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The program code may also be loaded onto a computer, other programmable data processing apparatus, or other devices to cause a series of operational steps to be performed on the computer, other programmable apparatus or other devices to produce a computer implemented process such that the program code which executed on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to 20 indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

The wireless connection may be a mobile telephone network. The wireless connection may also employ a WiFi network based on any one of the Institute of Electrical and Electronics Engineers (IEEE) 802.11 standards. Alternatively, the wireless connection may be a BLUETOOTH® connection. In addition, the wireless connection may employ a Radio Frequency Identification (RFID) communication including RFID standards established by the International Organization for Standardization (ISO), the International Electrotechnical Commission (IEC), the American Society for Testing and Materials (ASTM), the DASH7 Alliance, and EPCGlobal.

Alternatively, the wireless connection may employ a ZigBee connection 5 based on the IEEE 802 standard. In one embodiment, the wireless connection employs a Z-Wave connection as designed by Sigma Designs. Alternatively, the wireless connection may employ an ANT and/or ANT+ connection as defined by Dynastream Innovations Inc. of Cochrane, Canada.

The wireless connection may be an infrared connection including connections conforming at least to the Infrared Physical Layer Specification (IrPHY) as defined by the Infrared Data Association (IrDA). Alternatively, the wireless connection may be a cellular telephone network communication. All standards and/or connection types include the latest version and revision of the standard and/or connection type as of the filing date of this application.

The description of elements in each figure may refer to elements of proceeding figures. Like numbers refer to like elements in all figures, including alternate embodiments of like elements.

FIG. 1 illustrates a graphical representation of an interoperable medical code system 100 for securely managing medical orders and/or medical records with respect to a patient 180 within the medical environment. The system 100 includes a server 130 with a web interface for hosting a website and/or one or more database servers, wherein the server 130 may manage information relating to medical personnel, electronic prescribing software, third-party electronic prescription providers, pharmacies, and/or patients. The server 130 of the system 100 may create and allow access to created individual medical personnel files. The interoperable medical code system 100 described herein provides a secure multi-way communication between the server 130, a hub 105, a health care practitioner 110, a medical service provider 160, a pharmacy 125, an insurance provider 115, and a patient 180.

An electronic medical order generation application 120 at the health care practitioner 110 can be employed for generation of at least one medical order 190 with respect to the patient 180. The medical order 190 may comprise at least one of a prescription, practitioner notes, prescription data, test order data, test result data, treatment data, and file data for the patient 180. The electronic medical order generation application 120 may communicate the medical order 190 to the server 130 and/or hub 105 through the network 150.

In one embodiment, a health care practitioner 110 may generate the medical order 190 using the network 150 to access a web interface of the server 130 and/or hub 105. In addition, the patient 180 may access the server 130 and/or hub 105 using an electronic device 185 such as a mobile telephone, a tablet, and/or a computer.

An insurance provider 115 and/or pharmacy 125 may also communicate with the server 130 and/or hub 105 through the network 150. In addition, a medical service provider 160 may employ a medical order retrieval application 170 to communicate with the server 130 and/or hub 105 through the network 150.

The server 130 communicates with a centralized database 187. The centralized database 187 receives and stores the medical order 190 along with an interoperable medical code 140 for the patient 180 for future retrieval. The centralized database 187 may also store patient information for the patient 180. A medical order retrieval application 170 at a medical service provider 160 can be utilized to retrieve the medical order 190 for the patient 180 using the interoperable medical code 140 in order to view and deliver the prescribed services, tests, diagnostics, treatments, procedures, drugs and medical items, referred to hereafter as medical services, with respect to the patient 180. The physical copy, Short Message Service (SMS) and/or email instance of the medical order 190 with the interoperable medical code 140 can be provided to the patient 180 to permit him to obtain the medical services at any medical service provider 160. At least a portion of the interoperable medical code 140 may be encoded in a format selected from the group consisting of a two-dimensional optical code, a Quick Response (QR) code, a bar code, text, and a Universal Product Code (UPC).

The health care practitioner 110 at the electronic medical order generation application 120 may generate the medical order 190 and send the medical order 190 to any preferred medical service provider 160 requested by the patient 180. The users of the system 100 such as health care practitioners 110, medical service providers 160, insurance providers, therapy providers, test order service labs, specialists, Medicare units, and government departments may access the medical order 190 encoded by the interoperable medical code 140 using credentials obtained from the system 100.

The patient 180 can collect the medical services at the medical service provider 160. The medical service provider 160 may authenticate the interoperable medical code 140 with respect to the patient 180 and access the medical order 190 using the credentials. Also, the medical service providers 160 and patients 180 may directly collect the medical services at a non-preferred medical service provider 160 by providing a physical copy and/or electronic copy of the prescription 190 and/or medical order 190 with proper identification information. The non-preferred medical service provider 160 can verify the interoperable medical code 140 printed on the patient's medical order 190, and on decrypting the interoperable medical code 140 can issue the medical services to the patient 180. The system 100 therefore may allow the health care practitioners 110 to readily and securely exchange the medical order 190 and patient information directly with other health care providers 160. The system 100 also permits the medical practitioners 110 to send prescription, refill orders, dose changes etc. to a medical service provider 160 such as a mail-order pharmacy on-line by avoiding direct or telephonic interactions between the users of the system 100.

The interoperable medical code system 100 permits the patient 180 to receive medical services such as collecting prescribed drugs at a pharmacy 115 or any other medical service provider 160 at any location and time with proper authentication by the system 100. The medical service provider 160 may access the centralized database 187 using an access credential. Alternatively, the medical service provider 160 may log into the server 130 and/or hub 105 and access the patient information from the centralized database 187 using a patient identifier and an access credential. Access credentials may include user accounts and/or passwords. Biometric data, and the like.

The patient 180 may retrieve specific reports for the patient 180 from the centralized database 187 of the system 100. The patient 180 may access the centralized database 187 using an access credential. Alternatively, biometric data such as the patient's thumb print may be used to access into the centralized database 187 for accessing the medical records or authenticating records for medical service provider 160. By only allowing access to the system 100 with access credentials, the system 100 ensures high level of data secured by protecting sensitive medical records such as, HIV or drug test positive reports with respect to the patient 180.

The interoperable medical code system 100 may maintain the access details of access by the medical service provider 160 in an access log to archive security details. The electronic medical order generation application 120 at the medical practitioners 110 permits changes to the medical order 190 such as, dose, quantity and strength of medicine with respect to the patient 180 in the centralized database 187 of the medical order 190 of the patient 180. The electronic medical order generation application 120 also permits the health care practitioner 110 to disable the interoperable medical code 140 and/or the medical order 190 in response to commands from the health care practitioner 110. The system 100 permits the patient 180 to view a medical order 190 from centralized database 187 by using the interoperable medical code 140 without editing or deleting the record. The medical order 190 for the patient 180 can be viewed through centralized database 187 at different hierarchy levels depending upon security levels and access credentials for medical practitioners 110, medical service providers 160 and the patient 180.

The system 100 may include additional communications links, which may be any communications links suitable for communicating data, e.g., between the server 130, the electronic medical order generation application 120, the medical order retrieval application 170, and electronic devices 185 such as network links, dial-up links, wireless links, hard-wired links, satellite links, any other suitable communications links, or a combination of such links. In one embodiment, the communications with the server 130 are secure and may include an encryption function and only individuals having an access credential can access the system 100.

The centralized system 100 described herein provide effective multi-way means for communicating medical orders 190, through a network 150 such as the internet or other suitable communication methods. The system 100 may allow access by medical service providers 160 having an access credential. The system 100 is further configured for creating business accounts for medical service providers 160, healthcare practitioners 110, and/or third party electronic prescription providers or software, and configured for editing the accounts by authorized personnel.

The interoperable medical codes 140 and associated data may be encrypted to preserve privacy. Unfortunately, processing the encrypted data can greatly increasing computing requirements. The embodiments described hereafter employ a decryption map to rapidly identify the access credentials required to process the interoperable medical codes 140, greatly accelerating computation.

Figure 2A:
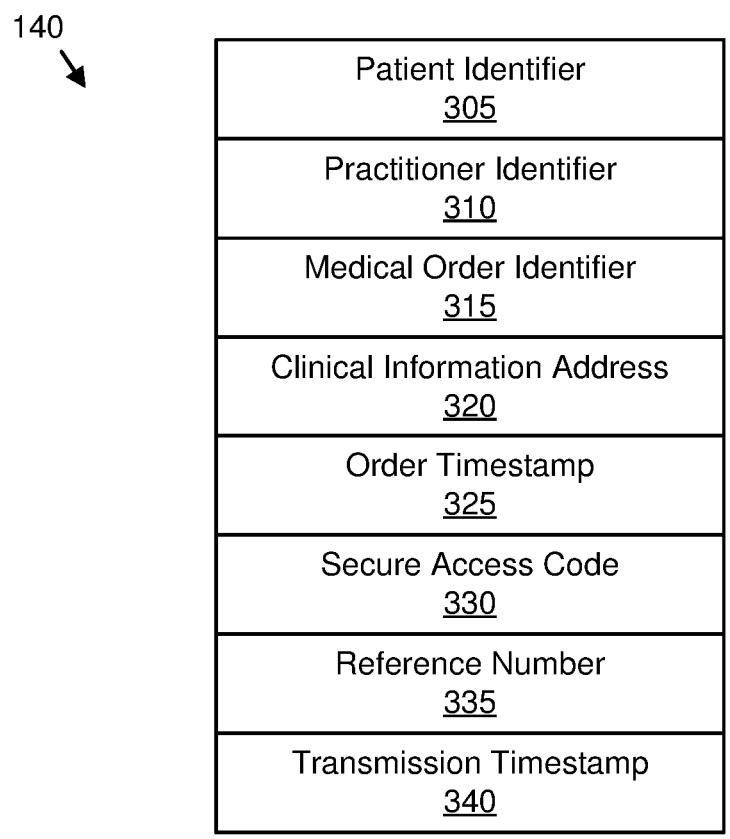
FIG. 2A is a schematic block diagram illustrating one embodiment of an interoperable medical code.

FIG. 2A is a schematic block diagram illustrating one embodiment of an interoperable medical code 140. The interoperable medical code 140 may be organized as a data structure in a memory. In addition, the interoperable medical code 140 may be encoded for transmission. The interoperable medical code 140 includes a patient identifier 305, a practitioner identifier 310, the medical order identifier 315, a clinical information address 320, an order timestamp 325, a secure access code 330, a reference number 335, and a transmission time stamp 340. The patient identifier 305, practitioner identifier 310, medical order identifier 315, clinical information address 320, order time stamp 325, secure access code 330, reference number 335, and transmission timestamp 340 may each comprise alphanumeric strings stored in a data field.

The patient identifier 305, practitioner identifier 310, medical order identifier 315, clinical information address 320, order time stamp 325, secure access code 330, reference number 335, and transmission timestamp 340 may each be separately encrypted. In one embodiment, the interoperable medical code 140 is also encrypted.

The patient identifier 305 may uniquely identify the patient 180. The patient identifier 305 may include a patient code, a patient name, a patient address, patient contact information, patient insurance information including Medicare and/or Medicaid information, and the like.

The practitioner identifier 310 may uniquely identify the health care practitioner 110. The practitioner identifier 310 may include a practitioner code, a practitioner name, and/or practitioner contact information.

Medical order identifier 315 is the medical order generated by the health care practitioner 110. The medical order identifier 315 may include but is not limited to one or more of a pharmaceutical prescription, a medical device prescription, a service order, a test order, and a diagnostic order. In one embodiment, the medical order identifier 315 comprises and/or references files including but not limited to radiology files, test results, test orders, and the like.

The clinical information address 320 may be a database index number, a Universal Resource Locator (URL), patient reference number, or combinations thereof that identify clinical information for the patient 180. The clinical information may comprise patient information including but not limited to health care practitioner reports, diagnostic test results, emergency medical reports, and the like.

The order timestamp 325 may indicate a time that the medical order identifier 315 was generated by the health care practitioner 110. The transmission timestamp 340 may indicate a time that the interoperable medical code 140 and/or medical order 190 are transmitted to the medical service provider 160.

The secure access code 330 may be used to access the interoperable medical code 140. For example, the user may enter the secure access code 330 to access the interoperable medical code 140. In one embodiment, the secure access code 330 is a secure key. The reference number 335 may be arbitrarily generated number identifying the interoperable medical code 140.

Figure 2B:
FIG. 2B is a schematic block diagram illustrating one alternate embodiment of an interoperable medical code.

FIG. 2B is a schematic block diagram illustrating one alternate embodiment of an interoperable medical code 140. The interoperable medical code 140 may be organized as a data structure in a memory. In addition, the interoperable medical code 140 may be encoded for transmission. In the depicted embodiment, the interoperable medical code 140 includes a decryption map 380, the patient identifier 305, the practitioner identifier 310, the medical order identifier 315, the order timestamp 325, the reference number 335, and the transmission timestamp 340.

The decryption map 380 supports rapid access to the information of the interoperable medical code 140. The decryption map 380 is described in more detail in FIG. 2C. The patient identifier 305, practitioner identifier 310, and medical order identifier 315 may reference the patient data, practitioner data, and/or medical data described in FIGS. 3A-C. In addition, the patient identifier 305, practitioner identifier 310, and medical order identifier 315 may comprise the patient data, practitioner data, and/or medical data.

Figure 2C:
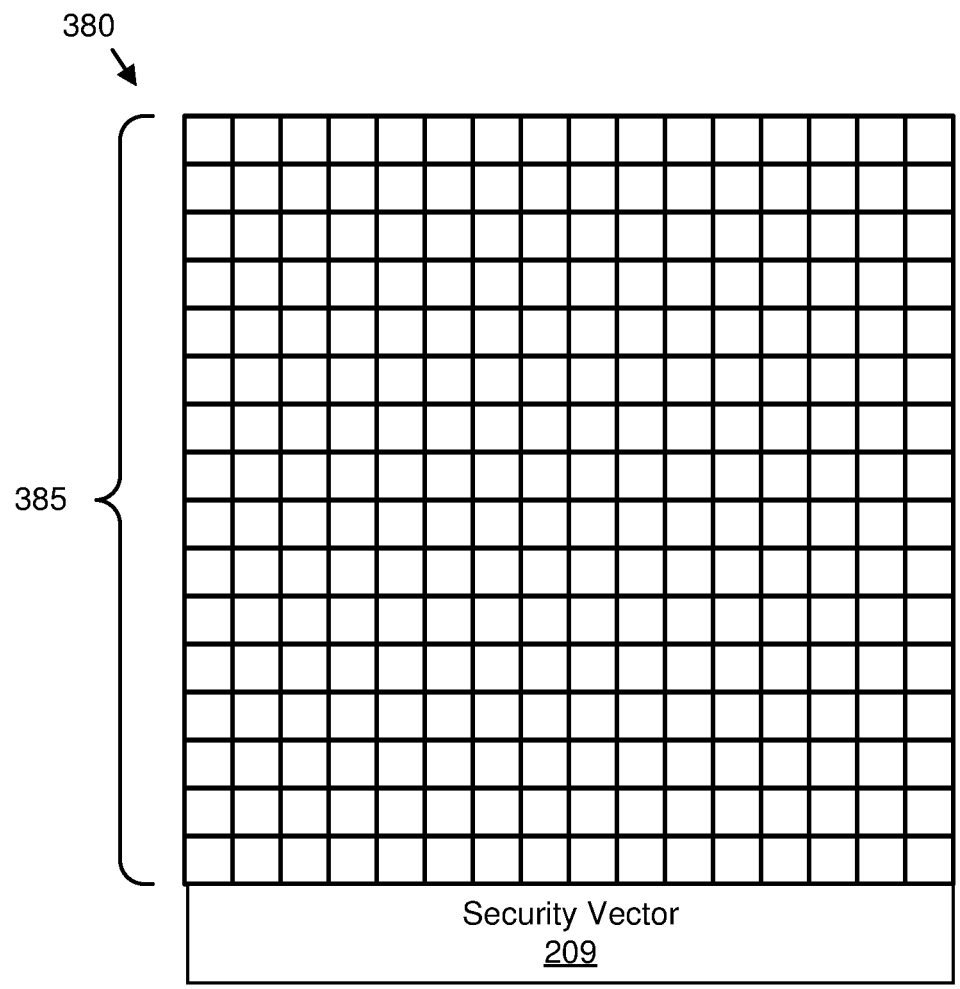
FIG. 2C is a schematic block diagram illustrating one embodiment of a decryption map.

FIG. 2C is a schematic block diagram illustrating one embodiment of the decryption map 380. In the depicted embodiment, the decryption map 380 includes a bit field 385 and a security vector 209. The bit field 385 includes binary bits in the range of 16 to 256 bits. The security vector 209 may include entity bits and security bits for each bit in the bit field 385 as will be described hereafter.

Decrypting encoded data can consume significant processing power. The decryption map 380 allows a processor to determine which encoded data must be decrypted and which access credentials must be used to decrypt the encoded data. As a result, the processor may rapidly determine if the required access credentials are available. If the required access credentials are not available, the processor may begin fetching the required access credentials.

The bit field 385 may indicate which of the entity bits in the security vector 209 are active. In one embodiment, the processor may determine from the bits of the bit field 385 alone if a specified access credential is required. For example, the processor may determine from a first bit if the access credential for Medicare related data is required.

In addition, the first bit may indicate that the processor should interrogate specified entity bits and security bits in the security vector 209 for additional information needed to decrypt and access data in the interoperable medical code 140. The security vector is described in more detail in FIG. 2D.

FIG. 2D is a schematic block diagram illustrating one embodiment of the security vector 209. In the depicted embodiment, the security vector 209 includes a plurality of pairs of entity bits 297 and security bits 299. Each pair may correspond to a bit in the bit field 385. The entity bits 297 may describe a patient 180, a healthcare practitioner 110, and/or a medical order 190. The security bits 299 may describe a security level and/or an access credential required to access information regarding the patient 180, the healthcare practitioner 110, and/or the medical order 190.

FIG. 2E is a schematic block diagram illustrating one embodiment of credential data 463. The credential data 463 may be organizes a data structure in a memory. In one embodiment, the credential data 463 is stored in the centralized database 187. In the depicted embodiment, the credential data 463 includes a plurality of entries, and each entry includes a credential identifier 461, a security level 427, and an access credential 465.

The access credential 465 may be used to encrypt data, decrypt data, or grant access to data. The access credential 465 may be a password, and encryption key, a decryption key, a PIN, and the like. The credential identifier 461 may identify the access credential 465. In addition, the credential identifier 461 may identify the entity for which the access credential 465 is employed, such as a patient 180, healthcare practitioner 110, and/or organization. The credential identifier 461 may further identify the type of data that is protected by the access credential 465. The security level 427 may specify protections associated with the access credential 465.

Figure 2F:
FIG. 2F is a schematic block diagram illustrating one embodiment of an access log.

FIG. 2F is a schematic block diagram illustrating one embodiment of an access log 467. The access log 467 may be organized as a data structure in a memory. In one embodiment, the access log 467 is stored in the centralized database 187. In the depicted embodiment, the access log 467 includes a plurality of entries, and each entry includes an accessor 471 and an access record 469. The access log 467 may record accesses to the interoperable medical code 140 and/or patient data, practitioner data, and medical order data by the accessor 471. The accessor 471 may be the medical service provider 160, the healthcare practitioner 110, the patient 180, the insurance provider 115, and/or the pharmacy 125.

FIG. 3A is a schematic block diagram illustrating one embodiment of patient data 201. The patient data 201 may be organized as a data structure in a memory and/or encoded for transmission. In the depicted embodiment, the patient data 201 includes a patient identifier 305, patient contact data 421, insurance data 423, pharmacy data 431, biometric data 433, an identifying document 435, and a hub identifier 437.

In addition, a security level 427 and a credential identifier 461 may be associated with each of the patient contact data 421, insurance data 423, pharmacy data 431, biometric data 433, identifying document 435, and hub identifier 437. The security level 427 may specify a level of protection for the corresponding data. The credential identifier 461 may indicate the access credential 465 required to access the corresponding data.

The patient contact data 421 may include a patient name, a patient address, a date of birth, a gender, a Social Security number, a voter registration number, a gun license number, a personal phone number, a personal email, a serial number, and the like. The insurance data 423 may include a Medicare number, a Medicaid number, an insurance number, and the like.

The pharmacy data 431 may identify one or more pharmacies at which the patient 180 may fill a prescription. The pharmacy data 431 may include a pharmacy name, an address, a telephone number, an email address, a URL, and the like.

The biometric data 433 may uniquely identify the patient 180. The biometric data 433 may include an image, a fingerprint, a retinal scan, or the like of the patient 180. The identifying document 435 may be an image of the driver's license, an electronic driver's license, an image of a passport, an electronic passport, an image of an insurance card, electronic insurance card, and the like.

The hub identifier 437 may identify the patient 180 to the hub 105. The hub identifier 437 may be an email address. Alternatively, the hub identifier 437 may be a user identifier.

FIG. 3B is a schematic block diagram illustrating one embodiment of practitioner data 203. The practitioner data 203 may be organized as a data structure in a memory and/or encoded for transmission. In the depicted embodiment, the practitioner data 203 includes the practitioner identifier 310, practitioner biometric data 439, organization data 441, public contact data 443, private contact data 445, license data 447, and the hub identifier 437.

A security level 427 and/or credential identifier 461 are associated with each of the practitioner identifier 310, practitioner biometric data 439, organization data 441, public contact data 443, private contact data 445, license data 447, and the hub identifier 437. The security level 427 may specify a level of protection for the corresponding data. The credential identifier 461 may indicate the access credential 465 required to access the corresponding data.

The practitioner biometric data 439 may include an image, a fingerprint, a retinal scan, or the like of the healthcare practitioner 110. The organization data 441 may include an organization name, an organization address, an organization URL, and the like for the organization that employs the healthcare practitioner 110.

The public contact data 443 may include contact information such as phone number, address, email address, and the like for the healthcare practitioner 110 that can be released to the patient 180. The private contact data 445 may include a phone number and/or email address for the healthcare practitioner 110 that may only be released to designated persons under designated circumstances. For example, the private contact data 445 may only be released to an attending physician in an emergency.

The license data 447 may include licenses, professional certifications, and the like for the healthcare practitioner 110. The hub identifier 437 may identify the healthcare practitioner 110 to the hub 105.

FIG. 3C is a schematic block diagram illustrating one embodiment medical order data 205. The medical order data 205 may be organized as a data structure in a memory and/or encoded for transmission. In the depicted embodiment, the medical order data 205 includes the medical order identifier 315, practitioner notes 449, prescription data 451, test order data 453, test result data 455, treatment data 457, and file data 459.

A security level 427 and/or credential identifier 461 are associated with each of the practitioner notes 449, prescription data 451, test order data 453, test result data 455, treatment data 457, and file data 459. The security level 427 may specify a level of protection for the corresponding data. The credential identifier 461 may indicate the access credential 465 required to access the corresponding data.

The practitioner notes 449 may include notes related to the medical order identifier 315 from the healthcare practitioner 110. The prescription data 451 may include a prescription medical order 190. In one embodiment, the prescription medical order 190 includes an electronic signature from the healthcare practitioner 110 that issues the prescription medical order 190. The prescription medical order 190 may be a first fill prescription medical order 190.

The test order data 453 may specify one or more tests to be performed on the patient 180. The test result data 455 may include the test results from the tests. The treatment data 457 may specify one or more courses of treatments for the patient 180. The file data 459 may include radiology files, patient records, and the like.

Figure 4:
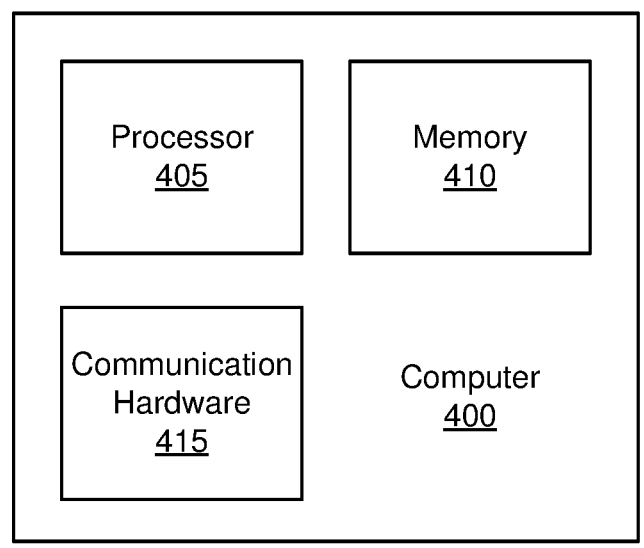
FIG. 4 is a schematic block diagram illustrating one embodiment of a computer.

FIG. 4 is a schematic block diagram illustrating one embodiment of a computer 400. The computer may be embodied in one or more of the electronic medical order generation app 120, the electronic device 185, the medical order retrieval application 170, the hub 105, and/or the server 130. In the depicted embodiment, the computer 400 includes a processor 405, a memory 410, and communication hardware 415. The memory 410 may include a semiconductor storage device, hard disk drive, an optical storage device, a micromechanical storage device, or combinations thereof. The memory 410 may store code. The processor 405 may execute the code. The communication hardware 415 may communicate with other devices such as the network 150.

Figure 5A:
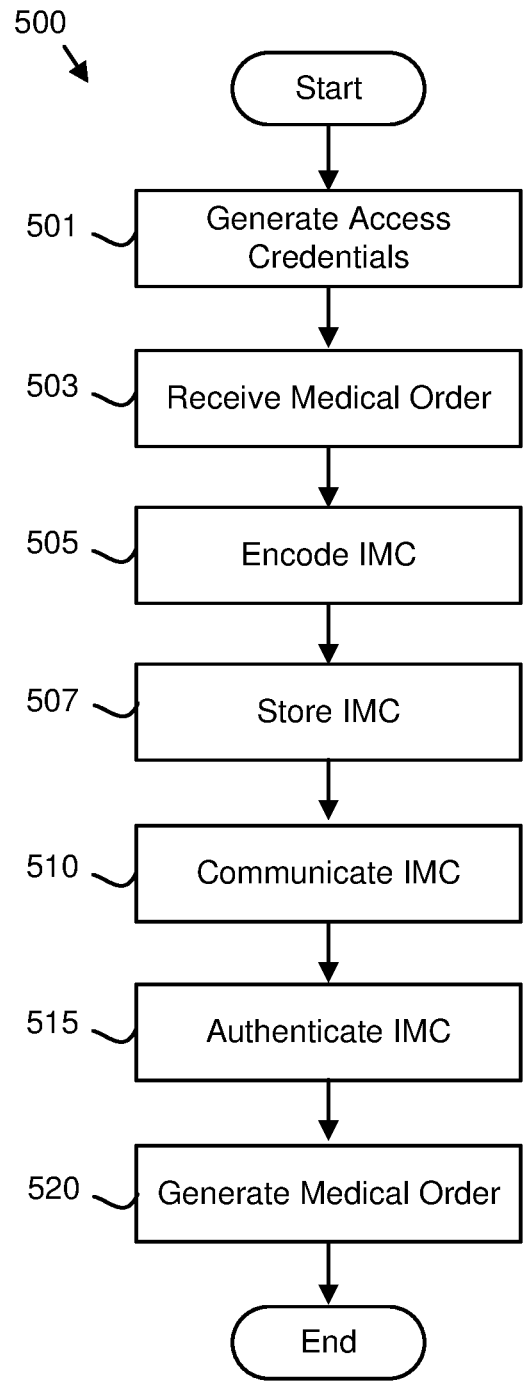
FIG. 5A is a schematic flow chart diagram illustrating one embodiment of a medical order generation method.

FIG. 5A is a schematic flow chart diagram illustrating one embodiment of a medical order communication method 500. The method 500 may encode the interoperable medical code 140 and generate the medical order 190 from the interoperable medical code 140. The method 500 may perform the functions of the system 100. The method 500 may be performed the processor 405.

The method 500 starts, and in one embodiment, one or more access credentials 465 are generated 101 for the centralized database 187. A patient 180, a healthcare provider 110, an insurance provider 115, a pharmacy 125, and/or a medical service provider 160 may provide 605 the access credentials 465 to the processor 405. In addition, a corresponding credential identifier 461 and security level 427 are identified for each access credential 465 and stored in the credential database 463.

The processor 405 may receive 503 a medical order 190. The medical order 190 may be generated by a healthcare practitioner 110 using the electronic medical order generation application 120 and/or an electronic device 185 such as a mobile telephone.

In one embodiment, the processor 405 encodes 505 the interoperable medical code 140 in response to receiving the medical order 190 from the health care practitioner 110. In one embodiment, the system 100 validates the health care practitioner 110 using the practitioner biometric data 439 such as a fingerprint scan before encoding the interoperable medical code 140. In addition, the processor 405 may encode the patient data 201, the practitioner data 203, and the medical order data 205.

The processor 405 may encrypt each of the patient identifier 305, practitioner identifier 310, medical order identifier 315, clinical information address 320, order time stamp 325, secure access code 330, reference number 335, and transmission timestamp 340. In addition, the processor 405 may encrypt the entire interoperable medical code 140. In one embodiment, the processor 405 generates a credential identifier 461 that corresponds to the patient 180, the healthcare practitioner 110, and/or a medical service provider 160. The processor 405 may further generate a security level 427 that corresponds to the medical order 190. The processor 405 may further retrieve an access credential 465 from the credential database 463 using the credential identifier 461 and the security level 427. In one embodiment, the processor 405 encrypts the interoperable medical code 140 or portions thereof with the access credential 465. Alternatively, the processor 405 may grant access to the interoperable medical code 140 or portions thereof in response to receiving the access credential 465.

In one embodiment, the processor 405 encrypts one or more of the patient contact data 421, insurance data 423, pharmacy data 431, biometric data 433, identify and document 435, identifier 437, practitioner biometric data 439, organization data 441, public contact data 443, private contact data 445, license data 447, practitioner notes 449, prescription data 451, test order data 453, test result data 455, treatment data 457, and file data 459 based on the corresponding security level 427. The patient contact data 421, insurance data 423, pharmacy data 431, biometric data 433, identify and document 435, identifier 437, practitioner biometric data 439, organization data 441, public contact data 443, private contact data 445, license data 447, practitioner notes 449, prescription data 451, test order data 453, test result data 455, treatment data 457, and file data 459 may be encrypted with the access credentials 465 that are stored in the centralized database 187. In one embodiment, the processor 405 generates a credential identifier 461 that corresponds to the patient 180, the healthcare practitioner 110, and/or a medical service provider 160. The processor 405 may further generate a security level 427 that corresponds to the data. The security level 427 may indicate whether encryption is required and/or the type of encryption. The processor 405 may encrypt and/or protect the data using the access credential 465. The processor 405 may generate the credential identifier 461 to specify how the corresponding data may be decrypted and/or accessed.

In addition, the processor 405 stores 507 the interoperable medical code 140 in the centralized database 187. The patient data 201, practitioner data 203, and/or medical order data 205 may be stored with the interoperable medical code 140. Alternatively, the patient data 201, practitioner data 203, and/or medical order data 205 may be stored separately from the interoperable medical code 140.

For example, the health care practitioner 110 may consult with the patient 180 and generate a medical order 190 that includes the interoperable medical code 140 using the electronic medical order generation application 120. The electronic medical order generation application 120 may store the interoperable medical code 140 and/or medical order 190 in the centralized database 187. In one embodiment, the processor 405 records the access to the centralized database 187 by the health care practitioner 110.

The processor 405 may further communicate 510 the interoperable medical code 140 and/or medical order 190.

The interoperable medical code 140 and/or medical order 190 may be communicated 510 to the patient 180 and/or medical service provider 160. In one embodiment, the electronic medical order generation application 120 communicates 510 the interoperable medical code 140 and/or medical order 190 to the medical service provider 160. Alternatively, the interoperable medical code 140 and/or medical order 190 may be communicated 110 from the server 130. The interoperable medical code 140 and/or medical order 190 may be communicated 110 as one or more of an email, a text, and a chat. In one embodiment, the interoperable medical code 140 is communicated 510 to a preferred medical service provider 160.

In one embodiment, the electronic medical order generation application 120 also generates a physical copy of the interoperable medical code 140. The interoperable medical code 140 may be printed as one or more of an alphanumeric string, a barcode, and a Quick Response (QR) code. In a certain embodiment, the interoperable medical code 140 and/or medical order 190 is printed on an embossed substrate. The patient 180 may present the physical copy of the interoperable medical code 140 to medical service provider 160 including a non-preferred medical service provider 160 to receive the medical services specified by the medical order identifier 315.

The processor 405 may further authenticate 515 the interoperable medical code 140. In one embodiment, the medical service provider 160 communicates the interoperable medical code 140 to the centralized database 187 and receives an authentication from the centralized database 187. Alternatively, the interoperable medical code 140 may be self-authenticating, allowing the medical service provider 160 to authenticate 515 the interoperable medical code 140 by decrypting one or more portions of the interoperable medical code 140 as described in FIG. 5C.

The processor 405 may further generate 520 the medical order 190 from the interoperable medical code 140. In one embodiment, the medical order 190 is generated 520 in response to authenticating the interoperable medical code 140. The medical service provider 160 may then provide the medical service specified in the medical order identifier 315 and the method 500 ends.

Figure 5B:
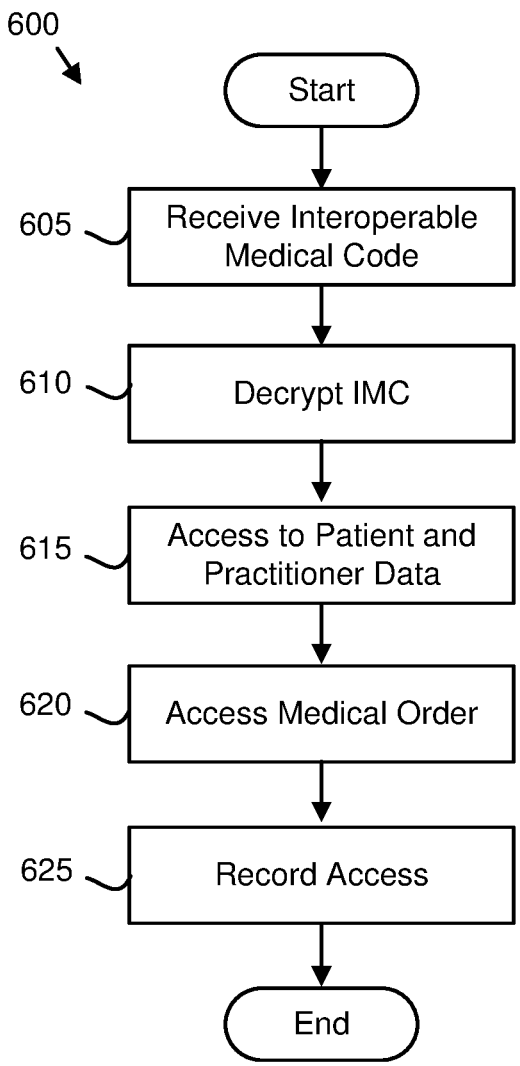
FIG. 5B is a schematic flow chart diagram illustrating one embodiment of a data access method.

FIG. 5B is a schematic flow chart diagram illustrating one embodiment of a data access method 600. The method 600 may access the interoperable medical code 140, patient data 201, practitioner data 203, and/or medical order data 205 as part of generating the medical order 140 of step 520 of FIG. 5A. The method 600 may be performed by use of the processor 405.

The method 600 starts, and the processor 405 may receive 605 the interoperable medical code 140. In one embodiment, the processor of the medical order retrieval application 170 receive 605 the interoperable medical code 140. Alternatively, the electronic device 185 may receive 605 the interoperable medical code 140. The interoperable medical code 140 may be received 605 via an electronic transmission such as an email, a text message, a packet transmission, and the like.

In a certain embodiment, if an emergency room possessed the full name and date of birth of the patient 180, and the healthcare practitioner identifier 310 for the patient's physician, or the hub identifier 437, the emergency room may access the patient information from the centralized database 187. As result, critical patient information is accessible even without the interoperable medical code 140.

The processor 405 may further decrypt 610 the interoperable medical code 140. The interoperable medical code 140 may be decrypted 610 with the secure access code 330. In addition, the interoperable medical code 140 may be decrypted 610 as described in FIG. 5C.

In response to decrypting 610 the interoperable medical code 140, the processor 405 may access 615 the patient identifier 305 and/or the patient data 201 associated with the interoperable medical code 140. In one embodiment, only the portions of the patient data 201 associated with a security level 427 appropriate for the medical order 190 may be accessed 615. In addition, only the portions of the patient data 201 for which the processor 405 has an access credential 465 may be accessed 615.

In addition, the processor 405 may access 615 the practitioner identifier 310 and/or the practitioner data 203. In one embodiment, only the portions of the practitioner data 203 associated with a security level 427 appropriate for the medical order 190 may be accessed 615. In addition, only the portions of the practitioner data 203 for which the processor 405 has an access credential 465 may be accessed 615.

The processor 405 may also access 620 the medical order identifier 315 and/or the medical order data 205. In one embodiment, only the portions of the medical order data 205 associated with a security level 427 appropriate for the medical order 190 may be accessed 620. In addition, only the portions of medical order data 205 for which the processor 405 has an access credential 465 may be accessed 620. In one embodiment, the healthcare practitioner 110 may disable the interoperable medical code 140 and the medical order identifier 315 using the command.

In one embodiment, the hub 105 and/or server 130 sends a physical copy of the needed data to a physical address specified by the public contact data 443 to access 620 the medical order data 205. An order to send an existing physical copy may be generated. Alternatively, a physical copy may be generated using a printer and sent to the physical address.

In one embodiment, the medical service provider 160 accesses 620 the medical order data 205 by modifying the patient data 201, the practitioner data 203, and/or the medical order data 205. The patient data 201, the practitioner data 203, and/or the medical order data 205 may be modified at the centralized database 187. For example, the medical service provider 160 may add practitioner notes 449, prescription data 451, test order data 453, test result data 455, treatment data 457, file data 459, and the like to the medical order data 205 in the centralized database 187.

In one embodiment, the processor 405 records 625 the access of the centralized database 187 by the medical service provider 160, patient 180, and/or healthcare practitioner 110, in an access log 467 and the method 600 ends.

The interoperable medical code 140 allows healthcare practitioners 110 to securely and safely communicate medical orders 190 to medical service providers 160. In addition, the interoperable medical code 140 may be used to securely access the patient information.

Figure 5C:
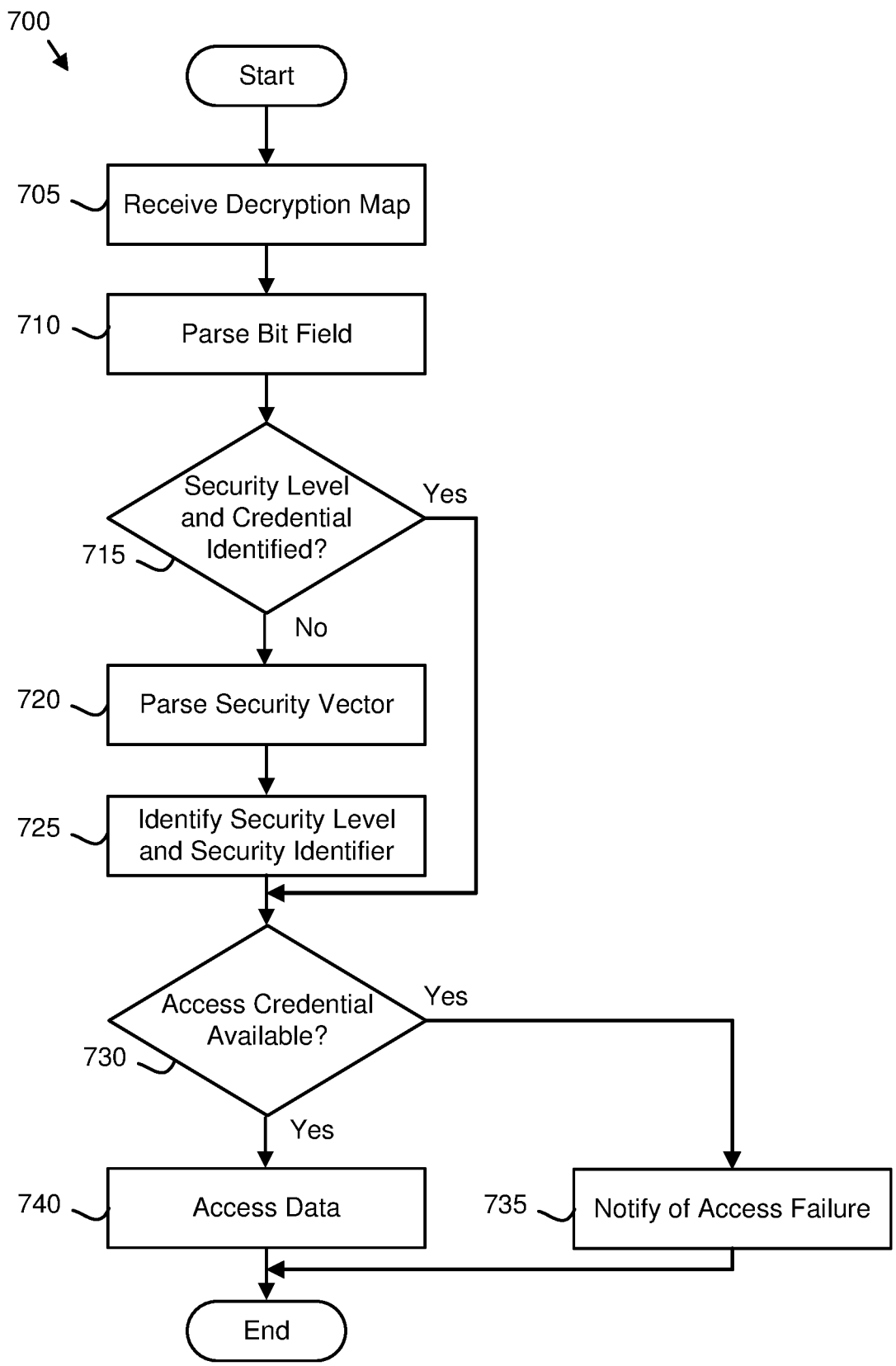
FIG. 5C is a schematic flow chart diagram illustrating one embodiment of a decryption method.

FIG. 5C is a schematic flow chart diagram illustrating one embodiment of a decryption method 700. The method 700 may decrypt the interoperable medical code 140 and associated data. The method 700 may be performed by the processor 405.

The method 700 starts, and in one embodiment, the processor 405 receives 705 the decryption map 380. The decryption map 380 may be received with the interoperable medical code 140. The processor 405 may parse 710 the bit field 385 of the decryption map 380 and determine 715 if the security level 427 and the credential identifier 461 for the needed data for the medical order 190 can be identified from the bit field 385. For example, a bit may identify a specific security level 427 and credential identifier 461. If the security level 427 and the credential identifier 461 can be identified, the processor 405 determines 730 if the access credential 465 for the needed data is available.

If the security level 427 and/or the credential identifier 461 cannot be identified, the processor 405 parses 720 the security vector 209. The processor 405 may use the bit field 385 to determine the security identifier 461 each pair of entity bits 297 and security bits 299 required to identify 725 the security level 427 and the credential identifier 461. In one embodiment, the processor 405 uses the entity bits 297 to generate the credential identifier 461 and the security bits 299 to generate the security level 427. Alternatively, the entity bits 297 and security bits 299 may be used as indexes to the credential identifier 461.

The processor 405 may determine 730 if the access credential 465 identified by the credential identifier 461 is available. For example, the processor 405 may have the access credential 465 associated with the bit field 385 and/or security level 427 and the credential identifier 461. In addition, the credential identifier 461 and the security level 427 may be used to request the access credential 465 for the needed data from the credential database 463. Alternatively, the entity bits 297 and security bits 299 may be used as indexes to determine 730 if the processor 405 has the access credential 465.

If the access credential 465 is not available, the processor 405 notifies 735 of the access failure and the method 700 ends. If the access credential 465 is available, the processor 405 uses the access credential 465 to decrypt the needed data and the method 700 ends. In one embodiment, the interoperable medical code may be validated with the access credential 465. In one embodiment, the processor 405 compares a password and/or PIN entered by the patient 180, medical service provider 160, pharmacy 125, and/or insurance provider 115 to the access credential 465 and grants access 740 to the data if the password and/or PIN match the access credential 465.

In one embodiment, the needed data is accessed 740 using the credential identifier 461 and the hub identifier 437. In one embodiment, the hub identifier 437 is used by the hub 105 to access the centralized database 187.

Figure 6A:
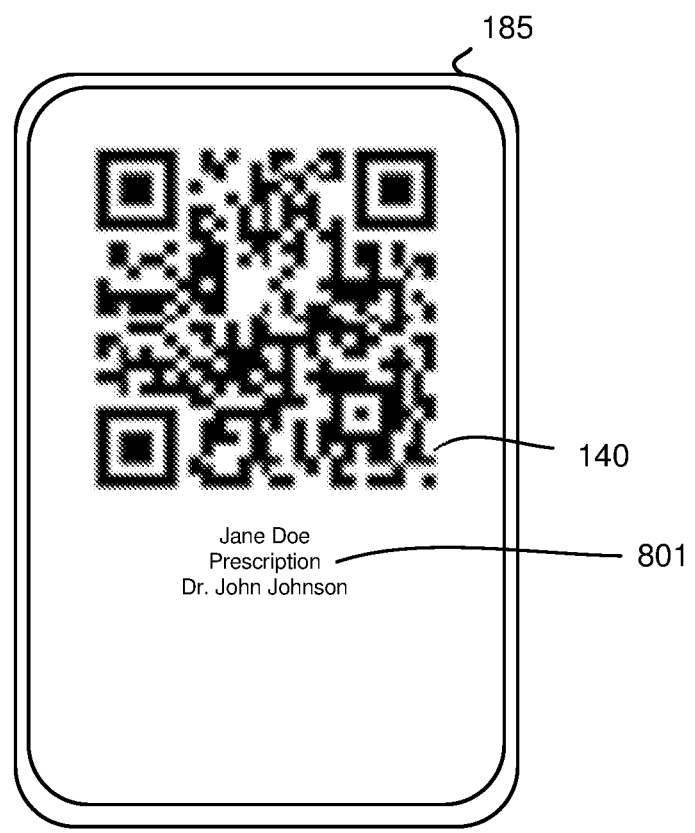
FIG. 6A is a drawing illustrating one embodiment of an interoperable medical code.

FIG. 6A is a drawing illustrating one embodiment of an interoperable medical code 140. In the depicted embodiment, the interoperable medical code 140 is displayed on electronic device 185. The user may present the electronic device 185 and the interoperable medical code 140 in order to fulfill a medical order 190. A medical service provider 160, pharmacy 125, and the like may fulfill the medical order 190 in response to receiving the interoperable medical code 140. In the depicted embodiment, a text summary 801 of the interoperable medical code 140 is also presented.

Figure 6B:
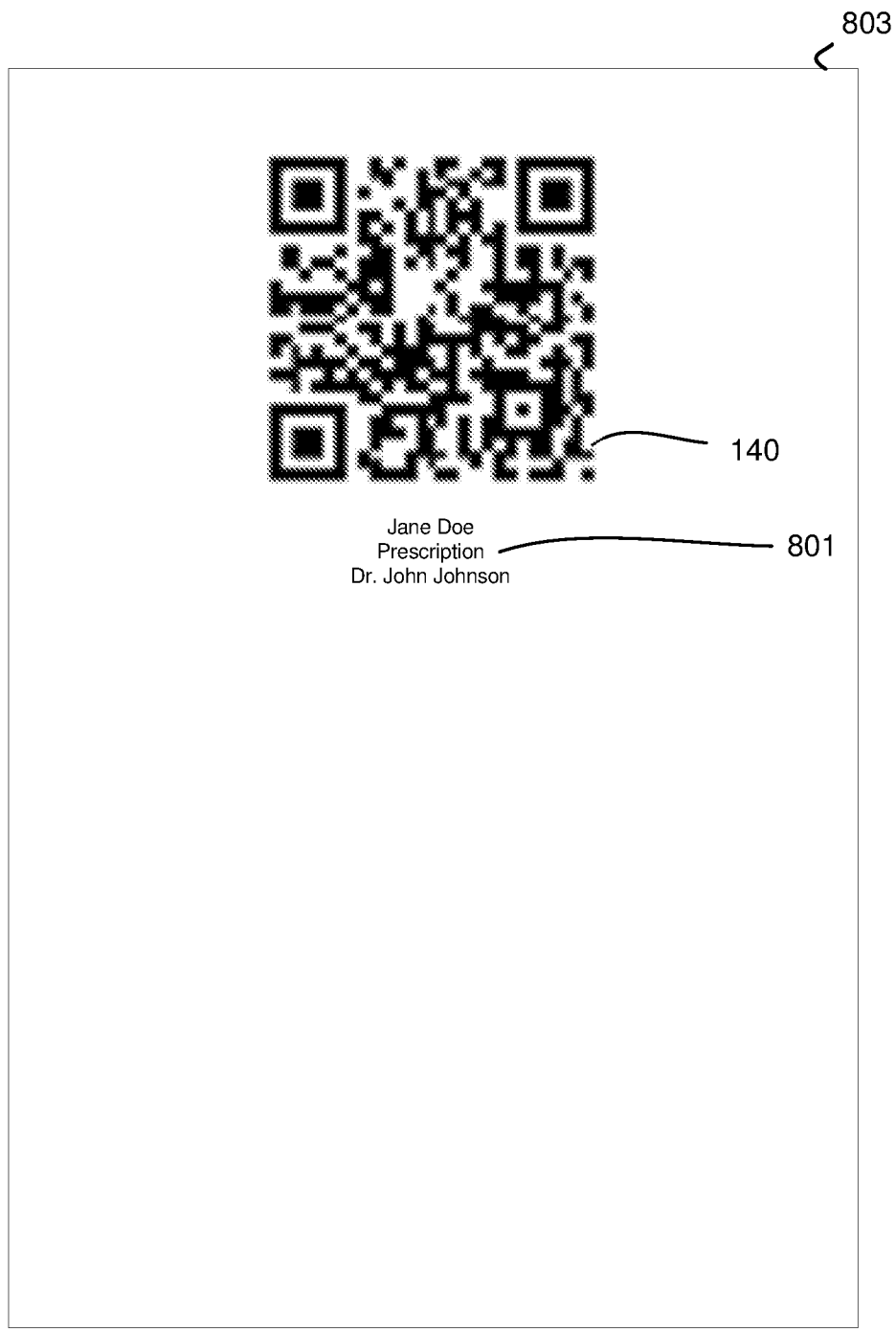
FIG. 6B is a drawing illustrating one alternate embodiment of an interoperable medical code.

FIG. 6B is a drawing illustrating one alternate embodiment of an interoperable medical code 140. In the depicted embodiment, the interoperable medical code 140 is a QR code printed on a physical copy 803 such as paper. The user may present the physical copy 803 with the interoperable medical code 140 to fulfill a medical order 190. A medical service provider 160, pharmacy 125, and the like may fulfill the medical order 190 in response to receiving the interoperable medical code 140. In the depicted embodiment, the text summary 801 of the interoperable medical code 140 is also printed on the paper 803.

Figure 6C:
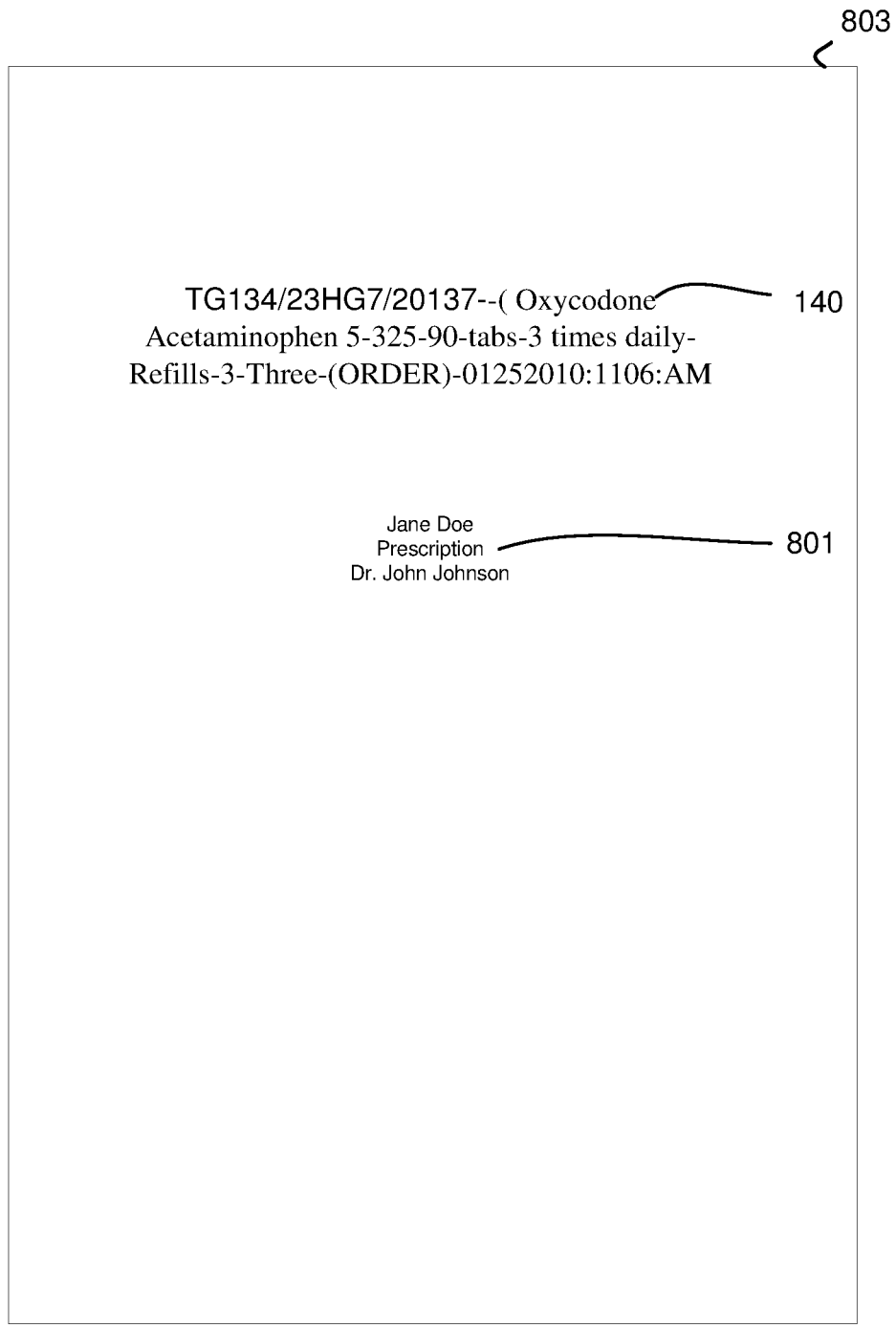
FIG. 6C is a drawing illustrating one alternate embodiment of an interoperable medical code.

FIG. 6C is a drawing illustrating one alternate embodiment of an interoperable medical code 140. In the depicted embodiment, the interoperable medical code 140 is text printed on a physical copy 803 such as paper. The user may present the physical copy 803 with the interoperable medical code 140 to fulfill a medical order 190. A medical service provider 160, pharmacy 125, and the like may fulfill the medical order 190 in response to receiving the interoperable medical code 140. In the depicted embodiment, the text summary 801 of the interoperable medical code 140 is also printed on the paper 803.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method comprising:

receiving, by use of a processor, an interoperable medical code, the interoperable medical code comprising a decryption map, a patient identifier for patient data, a practitioner identifier for practitioner data, and a medical order identifier for medical order data, wherein the decryption map comprises a bit field and a security vector that indicate access credentials required to access entries of the patient data, the practitioner data, and the medical order data, wherein each bit of the bit field corresponds to a pair of an entity bit and a security bit in the security vector, each entity bit describes a patient, a healthcare practitioner, and/or a medical order, each security bit describe a security level and/or an access credential required to access information regarding the patient, the healthcare practitioner, and/or the medical order, the patient data, the practitioner data, and the medical order data each comprise multiple entries, and each entry comprise a security level and a access credential, the patient data and the practitioner data each comprise a hub identifier;

identifying from the decryption map at least one access credential required to access one or more of the patient data, the practitioner data, and the medical order data required to fulfill the medical order by parsing the bit field of the decryption map, identifying the entity bits and the security bits in the security vector from the bit field, and identifying the at least one corresponding access credential from the entity bits and the security bits;

accessing the patient data, the practitioner data, and the medical order data required to fulfill the medical order using the at least one access credential, wherein a plurality of medical orders are accessed with accelerated computation; and fulfilling the medical order in response to accessing the patient data, the practitioner data, and the medical order data.

2. The method of claim 1, wherein the patient data, the practitioner data, and the medical order data required to fulfill the medical order are accessed using the at least one access credential and the hub identifier.

3. The method of claim 1, wherein the medical order data comprises at least one of a prescription, practitioner notes, prescription data, test order data, test result data, treatment data, and file data.

4. The method of claim 1, wherein the practitioner data comprises at least one of practitioner biometric data, organization data, public contact data, private contact data, license data, and the hub identifier.

5. The method of claim 1, wherein the patient data comprises at least one of patient contact data, insurance data, pharmacy data, biometric data, an identifying document, and the hub identifier.

6. The method of claim 1, wherein the interoperable medical code is received from one of an electronic prescription generation application, an e-prescription, a server, an electronic device, a hub, and a medical order retrieval application.

7. The method of claim 1, wherein at least a portion of the interoperable medical code is encoded in a format selected from the group consisting of a two-dimensional optical code, a Quick Response (QR) code, a bar code, text, and a Universal Product Code (UPC).

8. The method of claim 1, wherein accessing the patient data, the practitioner data, and the medical order data comprises modifying at least one of the patient data, the practitioner data, and the medical order data.

9. An apparatus comprising:
a processor;
a memory storing code executable by the processor to perform:
receiving an interoperable medical code, the interoperable medical code comprising a decryption map, a patient identifier for patient data, a practitioner identifier for practitioner data, and a medical order identifier for medical order data, wherein the decryption map comprises a bit field and a security vector that indicate access credentials required to access entries of the patient data, the practitioner data, and the medical order data, wherein each bit of the bit field corresponds to a pair of an entity bit and a security bit in the security vector, each entity bit describes a patient, a healthcare practitioner, and/or a medical order, each security bit describe a security level and/or an access credential required to access information regarding the patient, the healthcare practitioner, and/or the medical order, the patient data, the practitioner data, and the medical order data each comprise multiple entries, and each entry comprise a security level and an access credential, the patient data and the practitioner data each comprise a hub identifier;
identifying from the decryption map at least one access credential required to access one or more of the patient data, the practitioner data, and the medical order data required to fulfill the medical order by parsing the bit field of the decryption map, identifying the entity bits and the security bits in the security vector from the bit field, and identifying the at least one corresponding access credential from the entity bits and the security bits;
accessing the patient data, the practitioner data, and the medical order data required to fulfill the medical order using the at least one access credential, wherein a plurality of medical orders are accessed with accelerated computation, and
fulfilling the medical order in response to accessing the patient data, the practitioner data, and the medical order data.

10. The apparatus of claim 9, wherein the patient data, the practitioner data, and the medical order data required to fulfill the medical order are accessed using the at least one access credential and the hub identifier.

11. The apparatus of claim 9, wherein the medical order data comprises at least one of a prescription, practitioner notes, prescription data, test order data, test result data, treatment data, and file data.

12. The apparatus of claim 9, wherein the practitioner data comprises at least one of practitioner biometric data, organization data, public contact data, private contact data, license data, and the hub identifier.

13. The apparatus of claim 9, wherein the patient data comprises at least one of patient contact data, insurance data, pharmacy data, biometric data, an identifying document, and the hub identifier.

14. The apparatus of claim 9, wherein the interoperable medical code is received from one of an electronic prescription generation application, an e-prescription, a server, an electronic device, a hub, and a medical order retrieval application.

15. The apparatus of claim 9, wherein at least a portion of the interoperable medical code is encoded in a format selected from the group consisting of a two-dimensional optical code, a Quick Response (QR) code, a bar code, text, and a Universal Product Code (UPC).

16. A program product comprising a non-transitory computer readable storage medium that stores code executable by a processor to perform:
receiving an interoperable medical code, the interoperable medical code comprising a decryption map, a patient identifier for patient data, a practitioner identifier for practitioner data, and a medical order identifier for medical order data, wherein the decryption map comprises a bit field and a security vector that indicate access credentials required to access entries of the patient data, the practitioner data, and the medical order data, wherein each bit of the bit field corresponds to a pair of an entity bit and a security bit in the security vector, each entity bit describes a patient, a healthcare practitioner, and/or a medical order, each security bit describe a security level and/or an access credential required to access information regarding the patient, the healthcare practitioner, and/or the medical order, the patient data, the practitioner data, and the medical order data each comprise multiple entries, and each entry comprise a security level and an access credential, the patient data and the practitioner data each comprise a hub identifier;
identifying from the decryption map at least one access credential required to access one or more of the patient data, the practitioner data, and the medical order data required to fulfill the medical order by parsing the bit field of the decryption map, identifying the entity bits and the security bits in the security vector from the bit field, and identifying the at least one corresponding access credential from the entity bits and the security bits;
accessing the patient data, the practitioner data, and the medical order data required to fulfill the medical order using the at least one access credential, wherein a plurality of medical orders are accessed with accelerated computation, and
fulfilling the medical order in response to accessing the patient data, the practitioner data, and the medical order data.

* * * * *